United States Patent [19]
Leinders et al.

[11] Patent Number: 5,991,668
[45] Date of Patent: Nov. 23, 1999

[54] MEDICAL ELECTRICAL LEAD

[75] Inventors: Robert Leinders, Limbricht; Nicolaas Lokhoff, Kerkrade; Paulus Van Venrooij, Hoensbroek; Arnoldus Bakels, Simpelveld, all of Netherlands

[73] Assignee: Medtronic, Inc., Minneapolis, Minn.

[21] Appl. No.: 08/936,991

[22] Filed: Sep. 25, 1997

[51] Int. Cl.$^6$ .................................................. A61N 1/04
[52] U.S. Cl. ............................................................ 607/125
[58] Field of Search .......................... 600/381; 607/125, 607/119, 122, 123

[56] References Cited

U.S. PATENT DOCUMENTS

| | | | |
|---|---|---|---|
| 3,937,225 | 2/1976 | Schramm | 128/418 |
| 4,386,615 | 6/1983 | Sowton | 128/786 |
| 4,519,403 | 5/1985 | Dickhudt | 128/785 |
| 4,721,118 | 1/1988 | Harris | 128/785 |
| 4,913,164 | 4/1990 | Greene et al. | 128/785 |
| 5,179,962 | 1/1993 | Dutcher et al. | 128/785 |
| 5,238,007 | 8/1993 | Giele et al. | 607/126 |
| 5,489,294 | 2/1996 | McVenes et al. | 607/120 |

OTHER PUBLICATIONS

Bipolar Leads for Use with Permanently Implantable Cardiac Pacing Systems: A Review of Limitations of Traditional and Coaxial Configurations and the Development and Testing of New Conductor, Insulation, and Electrode Designs—G. Frank O Tyers et al. (Invited Review –Journal of Investigative Surgery, 10:1–15, 1997).

Four Chamber Pacing in Dilated Cardiomyopathy—S. Cazeau et al. (Pace, vol. 17, Nove. 1994, Part II).

*Primary Examiner*—Scott M. Getow
*Attorney, Agent, or Firm*—Thomas F. Woods; Harold Patton; Michael J. Jaro

[57] ABSTRACT

A transvenous lead specifically designed for coronary sinus implantation. In the preferred embodiment the lead features an electrode which is eccentricity placed along the lead body. Disposed on the opposite side of the lead body is a tine-like member to push or maintain the electrode into contact with the vessel wall. Because the electrode and tine-like member do not entirely block the cross sectional area of the vessel, blood flow through the vessel is not impeded. Through such a configuration electrical stimulation with the tissue comprising the left side of the heart may be accomplished. In alternative embodiments other mechanisms besides tine-like member are used to maintain the contact of the electrode with the vessel wall. In a still further alternative embodiment the eccentricity disposed electrode is positioned instead upon the tip of the tine.

51 Claims, 6 Drawing Sheets

MEDICAL ELECTRICAL LEAD

FIELD OF THE INVENTION

This invention relates to the field of body implantable medical device systems, and in particular to a body implantable medical device system which includes a medical electrical lead particularly designed for implantation into the coronary sinus.

BACKGROUND OF THE INVENTION

Modern electrical therapeutic and diagnostic devices for the heart, such as pacemakers, cardiovertors, and defibrillators, for example, require a reliable electrical connection between the device and a region of the heart. Typically, a medical electrical "lead" is used for the desired electrical connection.

One type of commonly used implantable lead is a transvenous lead. Transvenous leads are positioned through the venous system to attach or electrically connect at their distal end to the heart. At their proximal end, they are connected to typically an implantable pulse generator. Such leads normally took the form of a long, generally straight, flexible, insulated conductor. Among the many advantages of a transvenous lead is that it permits an electrical contact with the heart without physically exposing the heart itself, i.e., major thoracic surgery is not required.

The specific design of a transvenous lead used is often varied depending upon the region of the heart to which it is to be connected. For example, U.S. Pat. No. 4,402,330 of Lindemans discloses a body implantable lead in which the lead body has a J-curve and the distal electrode has a permanent bend. In such a manner, the lead is configured to electrically connect to the right atrium.

While such a lead has been found acceptable for electrically connecting and thus pacing the right atrium, the need exists for a transvenous medical electrical lead which may provide an electrical connection to the left atrium. Of course the left atrium cannot, at present, be transvenously accessed with a lead for chronic implantation due to the direction of blood flow and the present limitations of materials. To be precise, blood flows through the right side of the heart (atrium and ventricle), through the lungs, through the left side of the heart (atrium and ventricle) and then through the rest of the body, including the brain, before returning again to the right side of the heart. Implanted objects, however, often cause minor blood clots and thrombus to form in the blood. These may, on occasion, dislodge and be released into the bloodstream. Because the blood circulates directly from the left atrium and ventricle to the brain, any clots, however minor, could have serious consequences if they were to reach the brain, e.g. a stroke. In contrast, any clots released from an object implanted in the right side of the heart would simply travel to the lungs, where they would lodge without any serious risk. Thus at present, chronic transvenous leads may not be safely implanted within the left side of the heart.

In spite of the difficulties, there remains a great need to be able to electrically stimulate or sense or both the left side of the heart. The most obvious reason is the left side of the heart accounts for the majority of the heart's hemodynamic output. For example, the left ventricle has a greater wall thickness (10–20 mm as compared to 1–5 mm) than the right side. This, of course, is reasonable given that the left side of the heart must pump blood throughout the body while the right side only pumps blood through the lungs.

Because the left side is relatively more important for hemodynamic output, not surprisingly various pathologies may be better treated through stimulation on the left side of the heart. For example, in patients with dilated cardiomyopathy, electrical stimulation of both the right side and the left side of the heart has been shown to be of major importance to improve the patients well-being and manage heart failure. See, for example, Cazeau et al., "Four Chamber Pacing in Dilated Cardiomyopathy," PACE, November 1994, pgs. 1974–79. See also Brecker and Fontainem, St. et al., "Effects Of Dual Chamber Pacing With Short Atrioventricular Delay In Dilated Cardiomyopathy," Lancet November 1992 Vol. 340 p1308–1312; Xiao HB et al., "Effect Of Left Bundle Branch Block On Diastolic Function In Dilated Cardiomyopathy," Br. Heart J 1991, 66(6) p443–447; and Fontaine G et al, "Electrophysiology Of Pseudofunction," CI.Meere (ed.) Cardiac pacing, state of the art 1979, Pacesymp, 1979 Montreal.

At present there are several techniques for implanting a lead onto or into the left side of the heart. First, of course, is through general thoracic surgery; either via a median sternotomy; intercostal approach; or, in a more limited procedure, a subxiphoid approach. These procedures, however, involve major surgery which may be painful and dangerous for the patient, as well as extremely costly. The sub-xiphoid approach, moreover, only permits limited access to the anterolateral surface of the left ventricle and does not provide any access to the left atrium. Another approach used is to electrically access the left atrium is through the coronary sinus.

The coronary sinus, however, presents challenges in both implanting the lead in the proper position as well as ensuring the lead maintains sufficient electrical contact with the desired tissue. U.S. Pat. No. 5,423,772 of Lurie et at. discloses a coronary sinus catheter having three sections. Each section has varying degrees of flexibility, with the proximal reinforced section being stiffer than an intermediate section, the intermediate section being stiffer than the softened tip section. The catheter also is curved, with the curve beginning in the intermediate section, the curve further continuing into the softened tip section, where the radius of curvature decreases, i.e., the catheter becomes more curved closer to the tip. One drawback to such a design, however, is that the particular shape of the curve is not ideally suited for electrically accessing the left atrium. In addition, such a catheter is relatively complicated to manufacture due to the required reinforcing braid or other mends in the proximal reinforced section. Finally, such a catheter does not permit introduction of a stylet to assist in the placement of the catheter into the coronary sinus.

It is thus an object of the present invention to provide a medical electrical lead which is suitably shaped to provide an electrical connection through the coronary sinus to the left atrium or even the left ventricle.

A still further object of the present invention is to provide such a medical electrical lead which may be readily flexed during implantation to provide the ability to be introduced transvenously.

A still further object of the present invention is to provide a medical electrical lead having an electrode which may be securely contacted against the coronary sinus wall but which will not occlude the coronary sinus.

SUMMARY OF THE INVENTION

These and other objects are accomplished through the present invention. In one embodiment, the present invention comprises a transvenous lead specifically designed for coronary sinus implantation. In the preferred embodiment the lead features an electrode which is eccentricity placed along the lead body. Disposed on the opposite side of the lead body is a tine-like member to push or maintain the electrode into contact with the vessel wall. Because the electrode and tine-like member do not entirely block the cross sectional area of the vessel, blood flow through the vessel is not impeded. Through such a configuration electrical stimulation with the tissue comprising the left side of the heart may be accomplished. In alternative embodiments other mechanisms besides tine-like member are used to maintain the contact of the electrode with the vessel wall. The use of such a tine causes the electrode to be disposed against the wall of the vessel. In addition, the tine assists in preventing the lead from moving within the vessel, possibly moving down into a narrower portion of the vessel in which the lead is not properly sized for, such as the great cardiac vein, and thereby occluding blood flow.

BRIEF DESCRIPTION OF THE FIGS.

FIG. 9b is an end view of the lead shown in FIG. 9a.

FIG. 10 is a top view of the lead shown in FIG. 9a.

FIG. 13 is a top plan view of the lead shown in FIG. 12a.

It should be understood the drawings are not necessarily to scale.

DETAILED DESCRIPTION OF THE INVENTION

Figure 1:
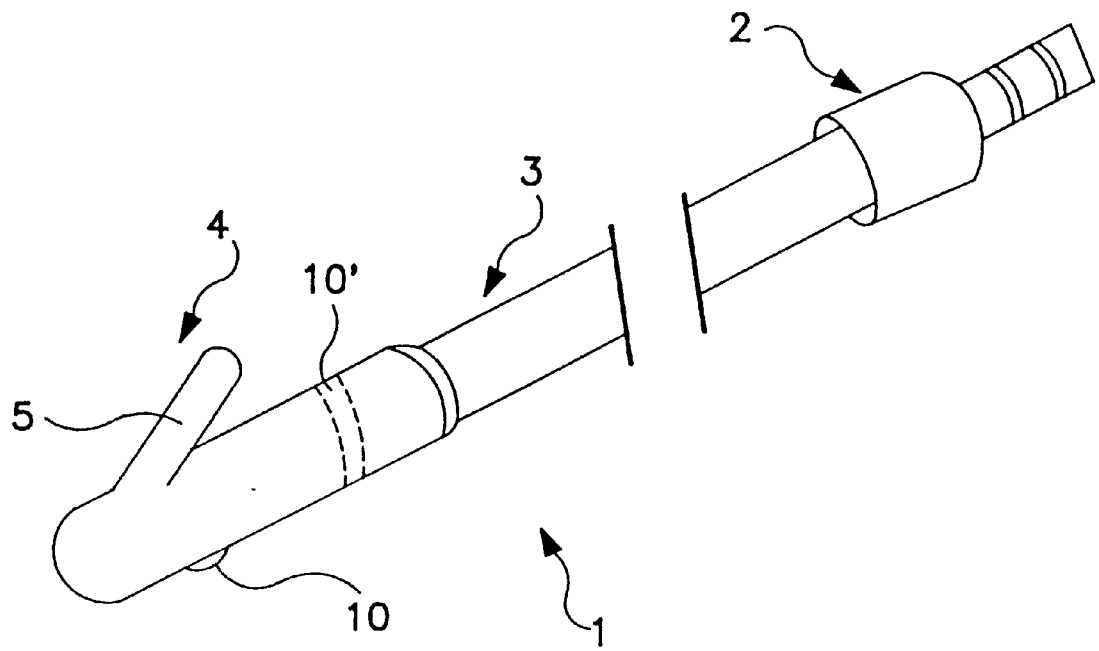
FIG. 1 is a perspective view of a lead according to the present invention.

FIG. 1 is a perspective view of a lead according to the present invention. As seen, lead 1 essentially has two portions: a connector portion 2 and a lead body portion 3. Distal end of lead body portion features an electrode/anchoring section 4. Connector portion is a standard connector used in the pacing area, such as an IS-1 UNI or an IS-1 BI. Of course, other connector designs may be used. Lead body portion 3 is coupled to connector portion 2 and further coupled to electrode/anchoring section 4. As seen, electrode/anchoring section features a tine 5 disposed on a first side of the lead and an electrode 10 disposed on the opposite side of the lead (in a bi polar configuration a second electrode 10' shown here in phantom is also positioned on electrode/anchoring section.)

Figure 2:
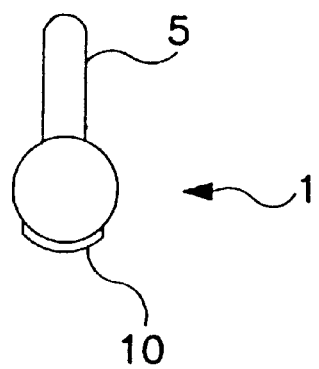
FIG. 2 is an end view of the lead shown in FIG. 1

FIG. 2 is an end view showing clearly the disposition of tine 5 opposite electrode 10. As seen in this view tine extends in a straight manner. It should be understood, however, tine may also extend in manners other than straight, such as curved or having an arc, for example.

Figure 3:
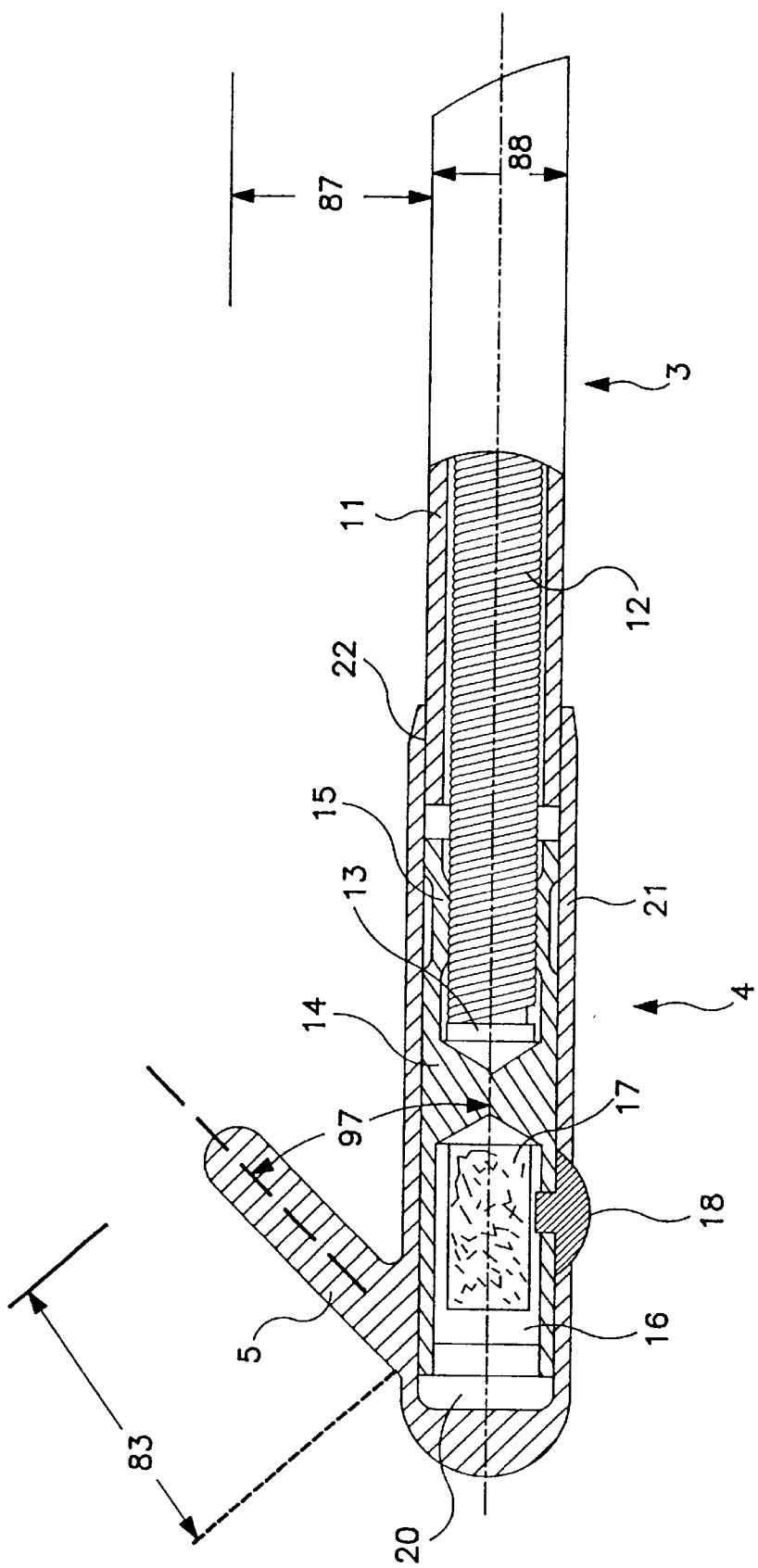
FIG. 3 is a cross-sectional view of the lead shown in FIG. 1.

FIG. 3 is a cross-sectional view showing the lead body portion joining into the electrode/anchoring portion. As seen, lead body portion 3 is constructed of an insulative sheath 11 surrounding a coiled conductor 12. Insulative sheath preferably is a biocompatible polymer such as silicone and coiled conductor preferably is a multi-filar coil of a biocompatible material such as MP35N. Of course, other materials may also be selected for each of these components, if desired. As seen, coiled conductor 12 has fitted, within its distal end, a crimping core 13. Core preferably is made of a platinum-iridium alloy. Surrounding the distal end of coiled conductor and crimp core is an electrode tube 14. As seen, tube is crimped in the area 15 to thereby mechanically as well as electrically join coiled conductor with tube. Tube preferably is formed also of a platinum-iridium alloy. As seen, tube further features a cavity 16 into which is disposed a monolithic controlled release device (MCRD) 17. MCRD is of standard construction and is designed to elute or dispense a drug from the electrode into the surrounding tissues, as is well known in the pacing art. In the preferred embodiment MCRD is a silicone rubber having the sodium salt of dexamethasone impregnated therein. A hole communicates through the tube from cavity to the outer portion of the lead. The hole is covered with an electrode cap 18. Electrode cap preferably is constructed using spherical platinum porous powder which has further a platinum black electroplate thereon as is well known in the pacing art. Disposed on the end of the electrode tube is electrode cap 20 preferably of the same material as insulative sheath. Fitted completely over the end of lead body and electrode tube is a tine part 21. Tine part preferably is glued along overlapping joint 22 to sheath 11. Tine part, moreover, further features a single tine 5 disposed at an approximately 45° angle. As seen, tine is disposed on a side opposite that of electrode. Tine extends at an angle 97 of between approximately 30 to 70 degrees relative to the center axis of the lead body, with 45degrees preferred. Tine has a length 83 which is between approximately 3 to 12millimeters in length, with 4 millimeters preferred. In such a manner tine extends upwards from lead body for a distance 87 as compared to the lead body diameter 88. In the preferred embodiment distance 87 is between approximately 2–8 millimeters and diameter 88 is between approximately 2–3 millimeters such that the distance 87 to diameter 88 ratio is between 1–4 to 1.

As discussed in more detail below, the provision of the tine permits the lead, when inserted into the coronary sinus to have the electrode brought in contact with the coronary sinus wall. Moreover, because the electrode is only a discrete point along the circumference of the lead body (as compared to ring electrode), the electrode may be positioned so as to point or contact the tissue of the heart most suitable for stimulation or sensing, or both. Most importantly however, is that due to the relative slight sizes of the tine length and width as related to the lead body diameters, such electrical contact to be achieved without occluding the vessel. Thus the dimension selected for the lead body and tine are essential to the proper performance of the lead within the coronary sinus.

Figure 4:
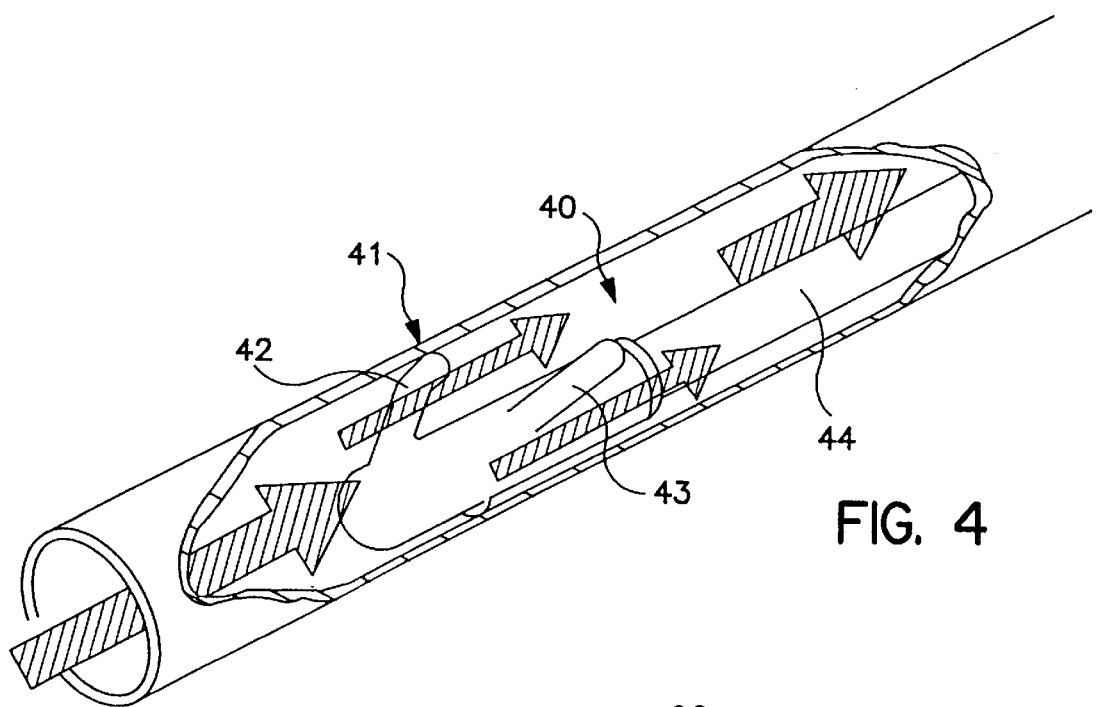
FIG. 4 depicts an alternate embodiment of the present invention.
Figure 5A:
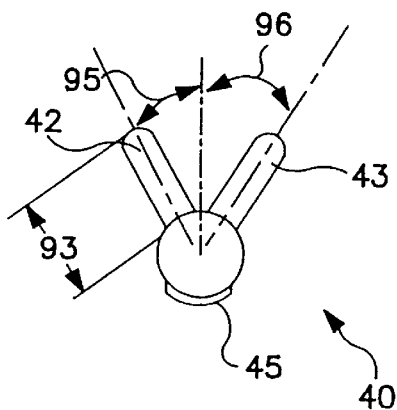
FIG. 5a is an end view of the alternate embodiment shown in FIG. 4.

FIG. 4 depicts an alternate embodiment of the present invention. As seen, in this embodiment the lead 40 is also designed for disposition or placement into the coronary sinus 41. In this embodiment, however, the lead features a pair of tines 42 and 43 to assist in anchoring the lead into the coronary sinus. As discussed above, the lead is designed so as to have no significant impact on the flow of blood through the coronary sinus or whatever vessel the lead is placed in. In the present figure this is depicted through lines 44 which represent the flow of blood FIG. 5A is an end view of the alternate embodiment shown in FIG. 4. As seen in this view, the lead 40 has tines 42 and 43 disposed in a symmetrical fashion about the lead body and opposite electrode 45. Tines are disposed at a radial angles 95 and 96 from the top of the lead body, preferably these radial angles are the same and are between approximately 15 and 90 with 30 degrees preferred for each. Or, with respect to the electrode, the tines are each disposed along the lead body at a radial distance between approximately 110–150 degrees opposite the electrode. Moreover each tine has a length 93 which is between approximately 3 to 5millimeters in length, with 4 millimeters preferred.

Figure 5B:
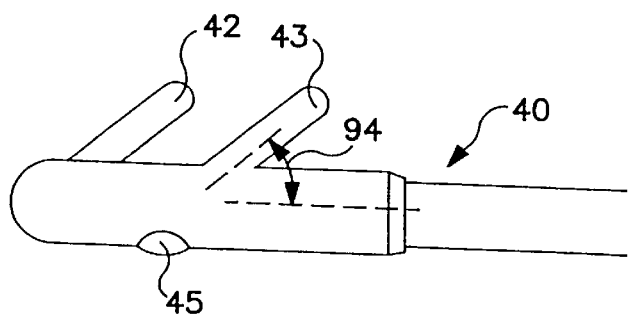
FIG. 5b shows a side plan view of the distal end of the lead

FIG. 5B shows a side plan view of the distal end of the lead and, in particular, details the longitudinal positioning of the tines which are staggered along the lead body and has electrode disposed there between. Both tines extends at an angle 94 of between approximately 30 to 70 degrees relative to the center axis of the lead body, with 45 degrees preferred. Although not shown, the construction of the alternate embodiment of the lead depicted in FIGS. 4 and 5 is exactly the same as that shown in FIG. 3 but for the addition of the additional tine along electrode/anchoring portion.

Figure 6:
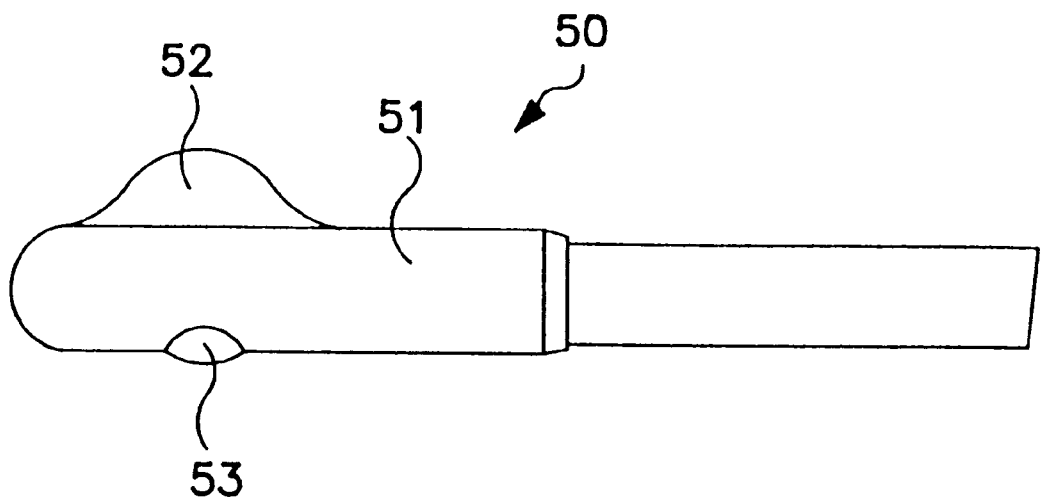
FIG. 6 shows a still further alternate embodiment of the present invention.

FIG. 6 shows a still further alternate embodiment of the present invention. In this embodiment lead 50 features a different design for electrode/anchoring section 51. In particular, in this design electrode/anchoring section features a wedge 52. Wedge is preferably constructed from the same material as that used in the rest of the electrode/anchoring section and is integrally therewith similar to the tine discussed above.

Figure 7:
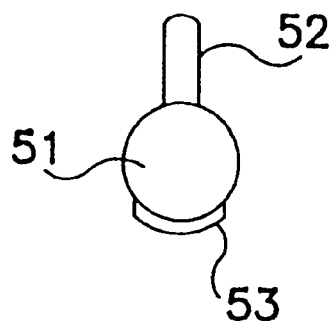
FIG. 7 is an end view of the embodiment shown in FIG. 6.

FIG. 7 is an end view of the embodiment shown in FIG. 6. As seen, wedge 52 is disposed opposite electrode 53. Other than the use of wedge, lead 50 is constructed in a similar fashion to the lead which is described in FIGS. 1–3, i.e. all the materials are the same and only a particular design of the wedge is different.

Figure 8:
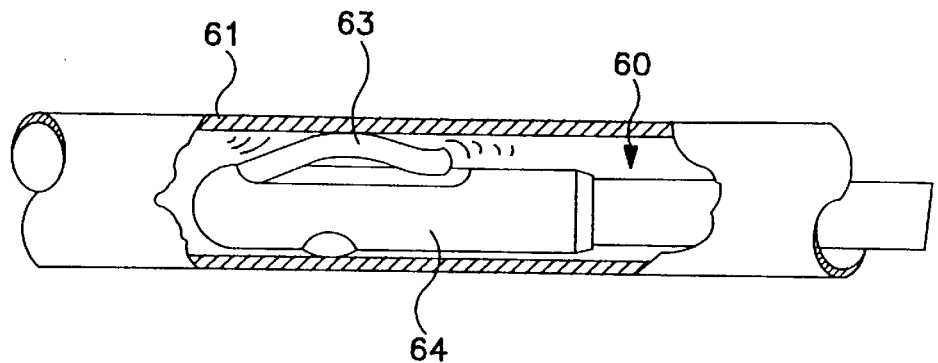
FIG. 8 shows a still further alternate embodiment of the present invention.

FIG. 8 shows a still further alternate embodiment of the present invention. In this embodiment lead 60 is essentially the same as the lead 1 described in FIGS. 1–3 above but for a different design on the electrode/anchoring section 64. In this view the lead 60 is disposed within the coronary sinus 61. In this design electrode/anchoring section features a bent-tail 63 disposed away from electrode/anchoring section so as to engage the wall of the coronary sinus.

Figure 9A:
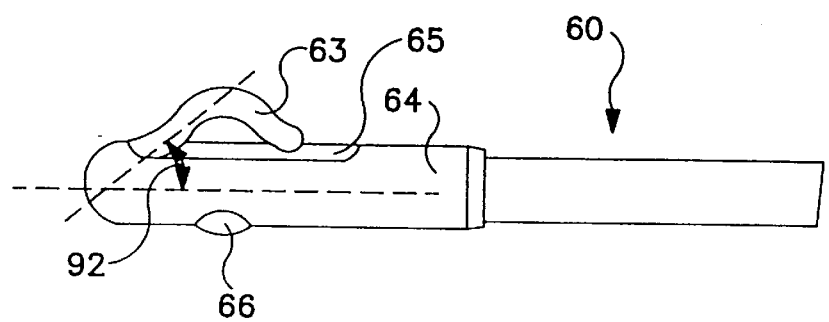
FIG. 9a is a plan view of the lead of the lead shown in FIG. 8

FIG. 9A is a plan view of the lead 60 showing the orientation of the bent-tail 63 of the electrode/anchoring portion. As seen, bent-tail comprises a solid piece of a polymer, the piece disposed at an angle 92 between approximately 30 to 60 degrees with 45 degrees preferred away from the electrode/anchoring section and further having a curve in the center so that the distal end of the bent-tail is disposed towards the electrode/anchoring portion. A furrow 65 is further provided in the electrode/anchoring section to accommodate the distal end of the bent-tail once the middle portion engages into the vessel wall to thereby fix the lead.

Figure 9B:
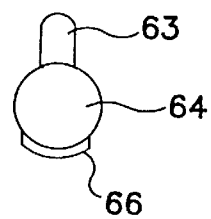

As best seen in FIG. 9B the electrode 66 is disposed on the opposite side of the lead from bent-tail. Electrode 66 is similar to that already discussed above in regards to FIGS. 1–3.

Figure 10:
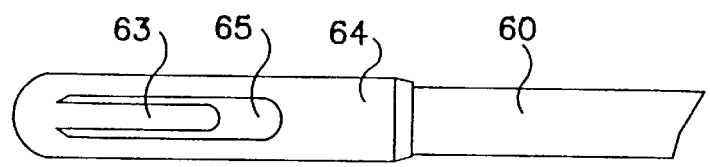

FIG. 10 is a top view of the lead 60 and, in particular, shows the orientation of the bent-tail and furrow. As seen furrow is slightly longer than the bent-tail to permit the accommodation of the distal end of the bent-tail into the furrow once the middle portion engages into the vessel wall and the bent tail is flattened. Moreover, there is a gap between the bent-tail and the furrow, i.e. the furrow is wider than bent-tail.

Figure 11:
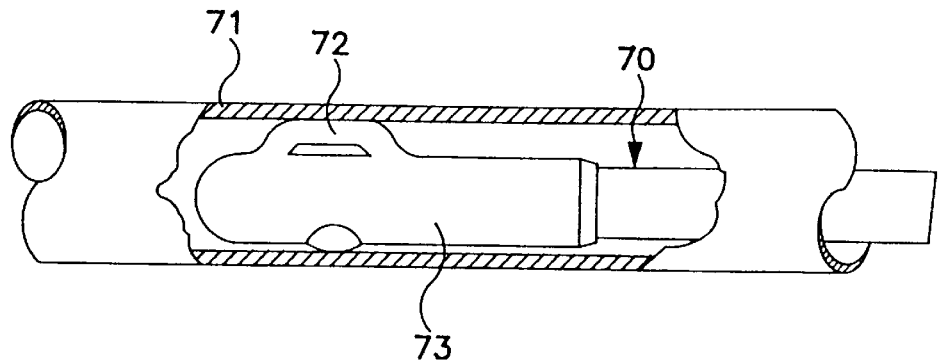
FIG. 11 shows a still further alternate embodiment of the present invention.

FIG. 11 shows a still further alternate embodiment of the present invention. As seen, lead 70 is positioned inside coronary sinus 71. In this embodiment lead 70 features a loop 72 along electrode/anchoring section 73 to thereby engage into the vessel wall and wedge or fix the lead in position.

Figure 12A:
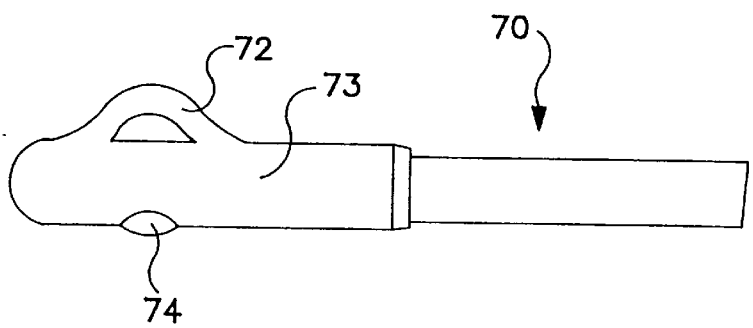
FIG. 12a is a side plan view of the lead shown in FIG. 11.

FIG. 12A is a side plan view of the lead shown in FIG. 11. As seen, loop 72 is circular in shape when not deformed at body structure, such as the vessel wall. Electrode/anchoring section further features electrode 74.

Figure 12B:
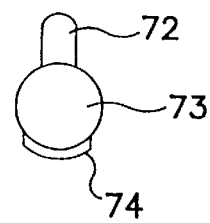
FIG. 12b is an end view of the lead shown in FIG. 11

As best seen in FIG. 12B electrode 74 is positioned opposite loop. Electrode 74 is similar to that already discussed above in regards to FIGS. 1–3.

Figure 13:
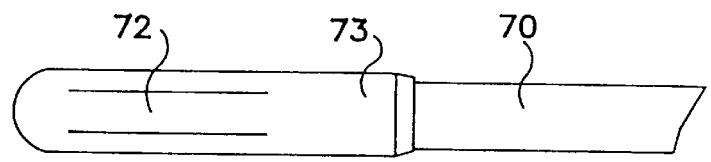

FIG. 13 is a top plan view of the lead shown in FIG. 12A. As seen in this view, loop 72 extends in a longitudinally parallel direction along electrode anchoring portion 73.

Each of the above described embodiments may further be provided with a coating of one or more various compounds or be surface treated to increase biocompatibility. Such coating may include heparin or other anti-thrombus agents, for example.

In an alternative design, the electrode may be fabricated without an MCRD, and instead the electrode may be treated with a very slightly soluble in water steroid, such as beclomethasone dipropionate anhydrous. Preferably the steroid is applied to the surface of the electrode which contacts tissue when implanted. Further details of such a coating process may be found in the copending U.S. patent application of Williams "Medical Electrical Lead" Ser. No. 081605,591, incorporated herein by reference.

It must be understood that the particular dimensions and ratios of the various lead components are crucial and essential to the effective operation of the present invention.

It is to be understood that the present invention is not limited to use only in pacing leads, and may be employed in the construction of may of various type of therapeutic and diagnostic devices, including defibrillation leads, intended to be disposed within the coronary sinus. In fact, for the purposes of this specification and claims, the term "lead" is used herein in its broadest sense and includes any stimulation lead or sensing lead, a combination thereof or any other elongated member, such as a catheter, which may usefully be introduced into a body. For purposes of illustration only, however, the present invention has been described in the context of transvenous pacing lead. Moreover, the present invention may be used in any of the various venous and arterial pathways along the heart or anywhere else within the body, thus the term "coronary sinus" is also used herein in its broadest sense and includes, without limitation, the great cardiac vein, as well as any other cardiac vessel.

Although a specific embodiment of the invention has been disclosed, this is done for purposes of illustration and is not intended to be limiting with regard to the scope of the invention. It is contemplated various substitutions, alterations and/or modifications may be made to the disclosed embodiment without departing from the spirit and scope of the invention. Such modifications may include substituting elements or components which perform substantially the same function in substantially the same way to achieve substantially the same result for those described herein.

What is claimed is:

1. A medical electrical lead comprising
   means for electrically coupling to a pulse generator;
   a lead body coupled to the means for electrically coupling, the lead body having a conductor having a first end and a second end and an insulator covering the conductor between the first end and the second ends the lead body having a circumference, the insulator being smooth along an exterior;
   an electrode coupled to the second end, the electrode positioned on a first side of the insulator along only a portion of the lead body circumference; and
   means for bringing the electrode in contact with a blood vessel wall, the means positioned on a second side of the insulator.

2. The medical electrical lead according to claim 1 further comprising the insulator having a blunted end portion.

3. The medical electrical lead according to claim 1 wherein the first side is opposite the second side.

4. The medical electrical lead according to claim 1 wherein the means for bringing the electrode in contact with a blood vessel wall comprise a member mounted to the insulator by a hinge.

5. The medical electrical lead according to claim 4 wherein the member is elastic and the hinge is elastic.

6. The medical electrical lead according to claim 4 wherein said member is a tine, the tine extending upwards from lead body for a first distance, the lead body having a lead body diameter, the ratio of the first distance to the lead body diameter being between approximately 1–4 to 1.

7. The medical electrical lead according to claim 4 wherein the member is elastic and the hinge is elastic.

8. The medical electrical lead according to claim 1 wherein the means for bringing the electrode in contact with a blood vessel wall comprises an asymmetric elastic rib having a first surface, the first surface extends beyond the exterior surface of the insulator a first distance.

9. The medical electrical lead according to claim 8 wherein the insulator has a first diameter, the first distance being at least equal in dimension to the first diameter.

10. The medical electrical lead according to claim 1 wherein the lead body has a pre set bend in a first portion.

11. The medical electrical lead according to claim 1 wherein the means for bringing the electrode in contact with a blood vessel wall further comprises the lead body has a dorsal side and a lateral side, a wedge protruding from the dorsal side.

12. The medical electrical lead according to claim 1 wherein the means for bringing the electrode in contact with a blood vessel wall comprises a first tine and a second tine, the first tine disposed along the lead body at a radial distance between approximately 110–150 degrees opposite the electrode, the second tine disposed along the lead body at a radial distance between approximately 110–150 degrees opposite the electrode.

13. The medical electrical lead according to claim 12 further comprising the first tine is disposed along the lead body at a first distance from the distal end, the second tine is disposed along the lead body at a second distance from the distal end, the first distance greater than the second distance.

14. The medical electrical lead according to claim 13 further comprising the first tine is disposed along the lead body at a first distance from the distal end, the second tine is disposed along the lead body at a second distance from the distal end, the first distance greater than the second distance.

15. A medical electrical lead comprising
    means for electrically coupling to a pulse generator;
    a lead body coupled to the means for electrically coupling, the lead body having a conductor having a first end and a second end and an insulator covering the conductor between the first end and the second end, the insulator being smooth along an exterior;
    an electrode coupled to the second end, the electrode positioned on a first side of the insulator; and
    wherein the lead body has a dorsal side and a lateral side, a wedge protruding from the dorsal side.

16. A medical electrical lead comprising:
    means for electrically coupling to a pulse generator;
    a lead body coupled to the means for electrically coupling, the lead body having a conductor having a first end and a second end and an insulator covering the conductor between the first end and the second end, the insulator being smooth along an exterior, the lead body having a circumference;
    an electrode coupled to the second end, the electrode positioned on a first side of the insulator along only a portion of the lead body circumference; and
    electrode contact means for bring the electrode in contact with a vessel wall, the electrode contact means positioned on a second side of the insulator.

17. The medical electrical lead according to claim 16 wherein the means comprise an elongate member disposed at an angle away from the lead body.

18. The medical electrical lead according to claim 17 wherein the means further comprise a furrow along the lead body corresponding to the elongate tubular member, the furrow having a width greater than a width of the elongate tubular member, the furrow having a length greater than a length of the elongate tubular member.

19. The medical electrical lead according to claim 16 wherein the elongate member has a bend in a center such that a distal end of the elongate member is position closer to the lead body than the center of the elongate member.

20. The medical electrical lead according to claim 16 wherein said elongate member is a tine, the tine extending upwards from lead body for a first distance, the lead body having a lead body diameter, the ratio of the first distance to the lead body diameter being between approximately 1–4 to 1.

21. A medical electrical lead comprising
    means for electrically coupling to a pulse generator;
    a lead body coupled to the means for electrically coupling, the lead body having a conductor having a first end and a second end and an insulator covering the conductor between the first end and the second end, the lead body having a circumference and a first diameter,
    an electrode cap coupled to the second end, the electrode cap positioned on a first side of the insulator along only a portion of the lead body circumference; and
    means for bringing the electrode cap in contact with a blood vessel wall, the means positioned on a second side of the insulator, wherein said means for bringing the electrode cap in contact with a blood vessel wall extends upwards from lead body for a first distance, the ratio of the first distance to the lead body diameter being between approximately 1–4 to 1.

22. The medical electrical lead according to claim 21 further comprising the insulator having a blunted end portion.

23. The medical electrical lead according to claim 21 wherein the first side is opposite the second side.

24. The medical electrical lead according to claim 21 wherein the means for bringing the electrode cap in contact with a blood vessel wall comprise a member mounted to the insulator by a hinge.

25. The medical electrical lead according to claim 21 wherein the means for bringing the electrode cap in contact with a blood vessel wall comprises an asymmetric elastic rib having a first surface, the first surface extends beyond the exterior surface of the insulator a first distance.

26. The medical electrical lead according to claim 25 wherein the insulator has a first diameter, the first distance being at least equal in dimension to the first diameter.

27. The medical electrical lead according to claim 21 wherein the lead body has a pre set bend in a first portion.

28. The medical electrical lead according to claim 21 wherein the means for bringing the electrode cap in contact with a blood vessel wall further comprises the lead body has a dorsal side and a lateral side, a wedge protruding from the dorsal side.

29. The medical electrical lead according to claim 21 wherein the means for bringing the electrode cap in contact with a blood vessel wall comprises a first tine and a second tine, the first tine disposed along the lead body at a radial distance between approximately 110–150 degrees opposite the electrode, the second tine disposed along the lead body at a radial distance between approximately 110–150 degrees opposite the electrode cap.

30. The medical electrical lead according to claim 21 wherein said means for bringing the electrode cap in contact with a blood vessel wall extends at an angle of between approximately 30 to 70 degrees relative to the lead body.

31. The medical electrical lead according to claim 21 wherein the first distance the means for bringing the electrode cap in contact with a blood vessel wall has a length which is between approximately 3 to 12 millimeters in length.

32. The medical electrical lead according to claim 21 wherein the lead body diameter is between approximately 2–3 millimeters.

33. The medical electrical lead according to claim 21 wherein the means for bringing the electrode cap in contact with a blood vessel wall extends upwards from the lead body for a distance between approximately 2–8 millimeters.

34. The medical electrical lead according to claim 21 wherein the tine has a length which is between approximately 3 to 12 millimeters in length.

35. The medical electrical lead according to claim 34 wherein the lead body diameter is between approximately 2–3 millimeters.

36. The medical electrical lead according to claim 34 wherein the tine extends upwards from the lead body for a distance between approximately 2–8 millimeters.

37. A medical electrical lead comprising
means for electrically coupling to a pulse generator;
a lead body coupled to the means for electrically coupling, the lead body having a conductor having a first end and a second end and an insulator covering the conductor between the first end and the second end, the lead body having a circumference and a first diameter;
an electrode cap coupled to the second end, the electrode cap positioned on a first side of the insulator along only a portion of the lead body circumference; and
means for bringing the electrode cap in contact with a blood vessel wall, the means positioned on a second side of the insulator, wherein the means for bringing the electrode in contact with a blood vessel wall comprises a first tine, the first member disposed along the lead body at a radial distance between approximately 110–180 degrees opposite the electrode.

38. The medical electrical lead according to claim 37 wherein said means for bringing the electrode cap in contact with a blood vessel wall extends upwards from lead body for a first distance, the ratio of the first distance to the lead body diameter being between approximately 1–4 to 1.

39. The medical electrical lead according to claim 37 further comprises a second tine, the second member disposed along the lead body at a radial distance between approximately 110–180 degrees opposite the electrode cap.

40. The medical electrical lead according to claim 39 wherein the first member is disposed along the lead body at a first distance from the distal end, the second member is disposed along the lead body at a second distance from the distal end.

41. The medical electrical lead according to claim 40 wherein the first distance greater than the second distance.

42. The medical electrical lead according to claim 40 wherein the first member is a wedge.

43. The medical electrical lead according to claim 40 wherein the first member is a tine.

44. A medical electrical lead comprising
means for electrically coupling to a pulse generator;
a lead body coupled to the means for electrically coupling, the lead body having a conductor having a first end and a second end and an insulator covering the conductor between the first end and the second end, the insulator being smooth along an exterior;
an electrode coupled to the second end, the electrode positioned on a first side of the insulator; and
means for bringing the electrode in contact with a blood vessel wall, the means positioned on a second side of the insulator wherein the means for bringing the electrode in contact with a blood vessel wall comprise a member mounted to the insulator by a hinge.

45. The medical electrical lead according to claim 46 wherein the member is elastic and the hinge is elastic.

46. A medical electrical lead comprising
means for electrically coupling to a pulse generator;
a lead body coupled to the means for electrically coupling, the lead body having a conductor having a first end and a second end and an insulator covering the conductor between the first end and the second end, the insulator being smooth along an exterior;
an electrode coupled to the second end, the electrode positioned on a first side of the insulator; and
means for bringing the electrode in contact with a blood vessel wall, the means positioned on a second side of the insulator wherein the means for bringing the electrode in contact with a blood vessel wall comprises an asymmetric elastic rib having a first surface, the first surface extends beyond the exterior surface of the insulator a first distance.

47. A medical electrical lead comprising
means for electrically coupling to a pulse generator;
a lead body coupled to the means for electrically coupling, the lead body having a conductor having a first end and a second end and an insulator covering the conductor between the first end and the second end, the insulator being smooth along an exterior;
an electrode coupled to the second end, the electrode positioned on a first side of the insulator; and
means for bringing the electrode in contact with a blood vessel wall, the means positioned on a second side of the insulator wherein the means for bringing the electrode in contact with a blood vessel wall further comprises the lead body has a dorsal side and a lateral side, a wedge protruding from the dorsal side.

48. A medical electrical lead comprising means for electrically coupling to a pulse generator;

a lead body coupled to the means for electrically coupling, the lead body having a conductor having a first end and a second end and an insulator covering the conductor between the first end and the second end, the insulator being smooth along an exterior;

an electrode coupled to the second end, the electrode positioned on a first side of the insulator; and means for bringing the electrode in contact with a blood vessel wall, the means positioned on a second side of the insulator wherein the means for bringing the electrode in contact with a blood vessel wall comprises a first tine and a second tine, the first tine disposed along the lead body at a radial distance between approximately 110–150 degrees opposite the electrode, the second tine disposed along the lead body at a radial distance between approximately 110–150 degrees opposite the electrode.

49. The medical electrical lead according to claim 48 further comprising the first tine is disposed along the lead body at a first distance from the distal end, the second tine is disposed along the lead body at a second distance from the distal end, the first distance greater than the second distance.

50. A medical electrical lead comprising:

means for electrically coupling to a pulse generator;

a lead body coupled to the means for electrically coupling, the lead body having a conductor having a first end and a second end and an insulator covering the conductor between the first end and the second end, the insulator being smooth along an exterior;

an electrode coupled to the second end, the electrode positioned on a first side of the insulator; and means for bringing the electrode in contact with a blood vessel wall, the means positioned on a second side of the insulator wherein said member is a tine, the tine extending upwards from lead body for a first distance, the lead body having a lead body diameter, the ratio of the first distance to the lead body diameter being between approximately 1–4 to 1.

51. A medical electrical lead comprising:

means for electrically coupling to a pulse generator;

a lead body coupled to the means for electrically coupling, the lead body having a conductor having a first end and a second end and an insulator covering the conductor between the first end and the second end, the insulator being smooth along an exterior an electrode coupled to the second end, the electrode positioned on a first side of the insulator; and electrode contact means for bring the electrode in contact with a vessel wall, the electrode contact means positioned on a second side of the insulator wherein the means comprise an elongate member disposed at an angle away from the lead body and wherein the means further comprise a furrow along the lead body corresponding to the elongate tubular member, the furrow having a width greater than a width of the elongate tubular member, the furrow having a length greater than a length of the elongate tubular member.

* * * * *